US00PP07950P

United States Patent [19]

Delbard

[11] Patent Number: Plant 7,950

[45] Date of Patent: Aug. 25, 1992

[54] ROSE PLANT — DELJACQ VARIETY

[75] Inventor: Georges Delbard, Malicorne, France

[73] Assignee: Georges Delbard Société Civile Agricole, Malicorne, France

[21] Appl. No.: 578,636

[22] Filed: Sep. 7, 1990

[51] Int. Cl.[5] ..... A01H 5/00

[52] U.S. Cl. ..... Plt./20

[58] Field of Search ..... Plt./20, 11

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms distinctive attractive double flowers which are Vermillion Hollandais on the inside and Rouge de Carthame on the outside. Such flowers are formed in abundance, are long lasting and comprise petals which detach cleanly. The plant exhibits an upright to bushy growth habit, forms vigorous vegetation, and is well suited for greenhouse forcing for cut flower production. Additionally, the plant is not particularly susceptible to diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety results from the crossing of the Tropicana variety (U.S. Plant Pat. No. 1,969) with an unnamed variety formed by the crossing of the Rome Glory variety (U.S. Plant Pat. No. 304) with the Impeccable variety (not patented in the United States). The male parent (i.e., the pollen parent) was an unnamed variety formed by the crossing of the Spartan variety (U.S. Plant Pat. No. 1,357) with the Baccara variety (U.S. Plant Pat. No. 1,367).

The parentage of the new variety can be summarized as follows:

[TROPICANA × (ROME GLORY × IMPECCABLE)] × (SPARTAN × BACCARA).

The seeds resulting from the above pollination were sown and 387 plantlets were obtained which were physically and biologically different from each other. Selective study resulted in the identification of a single plant of the new variety.

It was found through careful study that the new variety of the present invention can be characterized by the following combination of characteristics:

(a) from a physical point of view it forms bronze green mature wood, assumes an upright to bushy growth habit, and forms attractive double flowers with consistent petals which are Vermillion Hollandais on the inside and Rouge de Carthame on the outside, and (b) from the biological point of view it forms vigorous vegetation, produces flowers in abundance, exhibits the ability readily to be forced, is not particularly susceptible to diseases, and forms long lasting flowers comprising petals which detach cleanly.

The new variety well meets the needs of the horticultural industry and is particularly well suited for the production of long-lasting cut flowers.

The new variety has been found to undergo asexual propagation and can be readily reproduced by conventional routes such as budding (i.e., eye grafting), the use of cuttings, and micropropropagation in artificial media. Asexual propagation by the above-mentioned methods as performed in France has demonstrated that the characteristics of the new variety are strictly transmissible from one generation to another and appear to be firmly fixed.

The new variety has been named the Deljacq variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass at Hyéres, France.

FIG. 1 illustrates a specimen of a young shoot;

FIG. 2 illustrates a specimen of a floral bud at the opening of the sepals;

FIG. 3 illustrates a specimen of a floral bud at the opening of the petals;

FIG. 4 illustrates a specimen of a flower in the course of opening;

FIG. 5 illustrates a specimen of an open flower — plan view — obverse;

FIG. 6 illustrates a specimen of an open flower — plan view — reverse;

FIG. 7 illustrates a specimen of a fully open flower — plan view — obverse;

FIG. 8 illustrates a specimen of a fully open flower — plan view — reverse;

FIG. 9 illustrates a specimen of a floral receptacle showing the arrangement of the stamens and pistils;

FIG. 10 illustrates a specimen of a floral receptacle showing the arrangement of the pistils (sepals and stamens removed);

FIG. 11 illustrates a specimen of a flowering stem;

FIG. 12 illustrates a specimen of a main branch;

FIG. 13 illustrates a specimen of a leaf with three leaflets — plan view — upper surface;

FIG. 14 illustrates a specimen of a leaf with five leaflets — plan view — upper surface;

FIG. 15 illustrates a specimen of a leaf with seven leaflets — plan view — upper surface; and FIG. 16 illustrates a specimen of a leaf with seven leaflets — plan view — under surface.

DETAILED DESCRIPTION

The chart used in the identification of the colors is that of The Royal Horticultural Society (R.H.S. Colour Chart). The description is based on the observation of plants grown under glass at Hyéres, France. The coloration in common terms sometimes also is provided.

Class: Hybrid Tea

Plant:

*Height.*—Plants which were pruned to a height of 85 cm. produce floral stems having a length of approximately 40 to 60 cm.

*Habit.*—Upright to bushy.

Branches:

*Color.*—Young shoots: when approximately 20 cm. long exhibit a weak anthocyanin coloration having a bronze hue. Such coloration commonly approximates that of Greyed-Purple Group 183B with some brown-green coloration. Floral stems: Yellow-Green Group 146A shaded with bronze coloration. Mature wood: bronze green, Green Group 137B and 137C.

*Thorns.*—Configuration: concave upper and lower surfaces. Quantity: few which are 5 mm. or less in length, and an average number which are greater than 5 mm. in length. Color: when present on young sheets having a length of approximately 20 cm., Greyed-Purple Group 183A and 183B; when present on floral stems, Greyed-Orange Group 176A; and when present on mature wood, Greyed-Orange Group 165A and 165B.

*Petiole.*—Color on young shoots: Greyed-Purple Group 183A on upper and under surfaces. Color on mature wood: Yellow-Green Group 146A on upper surface, and Yellow-Green Group 146B on under surface.

*Leaflets.*—Number: commonly 3, 5, and 7. Size: medium to large. Shape: oval as illustrated, and convex with a weak margin undulation. Serration: single and regular. Texture: consistent. Color on young shoots: bronze with brown and purple on upper surface, and Greyed-Purple Group 183C on under surface. Color on floral stems: Green Group 137A on upper surface, and Yellow-Green Group 147B on under surface. Color on mature wood: Yellow-Green Group 147A on upper surface, and Yellow-Green Group 147B on under surface. General appearance: a weak glossiness commonly is present on the upper surface of the leaflets. Terminal leaflets: medium to long in length and width, have a rounded base, and are borne on petioles of long length.

Inflorescence:

*Number of flowers.*—Generally one per stem when grown in forced culture under greenhouse conditions.

*Peduncle.*—A medium number of hairs or prickles is present, and the coloration is Yellow-Green Group 145A.

*Sepals.*—Configuration: relatively long in length, with extensions of average length. Color: Yellow-Green Group 146D to Yellow-Green Group 147A on upper surface, and Yellow-Green Group 146C on under surface.

*Buds.*—Shape: ovate in longitudinal section just before the opening of the sepals.

*Flower.*—Time: average time to begin flowering. Shape: double, when fully open irregularly round when viewed from above, a generally flattened convex upper surface when viewed from the side, and a generally flattened convex under surface when viewed from the side. Diameter: approximately 75 to 95 mm. when fully open. Petal size: at second row from outside approximately 40 to 50 mm. in length, and approximately 53 to 60 mm. in width. Petal shape: the first 2 to 3 well-developed outermost petals tend to be of a transverse elliptic configuration, the margins possess weak reflexing with weak margin undulation and include a yellowish unguis on both surfaces. Petal color: the middle and marginal zones of the inner side are Vemillion Hollandais and approximate Red Group 40A, the middle and marginal zones of the outer side are Rouge de Carthame and approximate Red Group 41A, a very small spot on the inner side tends to be Yellow Group 13B to 13C, and a very small spot on the outer side tends to be Yellow Group 11C and 11D. Fragrance: slight. Lasting quality: long. Petal number: approximately 32 to 40 on average. Petal drop: good. Stamens: commonly number approximately 150, and are regularly arranged around pistils. Filaments: length is medium, most possess anthers, and the predominant coloration is orange-yellow. Anthers: medium in size, tend to open at substantially the same time, and the immature coloration approximates Yellow-Orange Group 21A. Pollen: is yellow in coloration and is provided in normal quantity. Pistils: commonly number approximately 135. Sitgmas: generally of approximately the same height as the anthers, and the coloration is pale yellow and approximates that of Yellow Group 10C and 10D. Styles: average in length, predominately pink in coloration with an average concentration of pubescence on the upper one-half. Receptacle: medium in size, approximately 23 mm. in diameter, and in longitudinal section, it is in the shape of a pitcher. Seeds: medium in size and commonly number approximately 16 to 30.

Development:

*Vegetation.*—Vigorous.

*Blooming.*—Very abundant and almost continuous.

*Resistance to diseases.*—Good.

*Aptitude to forcing.*—Excellent.

Generally one flower per stem is formed when the new variety is grown under forced culture conditions in a greenhouse. However, even under such conditions the first axillary eye below the flower may also develop into a cluster of approximately 3 to 5 flowers at a frequency of approximately 20 to 30 percent of the time. When grown outside, the new variety commonly forms flowers in clusters of approximately 3 to 5 flowers at a frequency of approximately 80 percent of the time.

Each of the parent varieties of the Deljacq variety forms blossoms of a different coloration than that of the new variety of the present invention. For instance, the Tropicana variety forms more orange blossoms than the Deljacq variety, the Rome Glory variety forms pure medium red blossoms; the Impeccable variety forms pure purple-red blossoms; the Spartan variety forms dark orange blossoms which lack the luminosity and brightness of the Deljacq variety; and the Baccara variety forms blossoms which are more red and darker.

I claim:

1. A new and distinct variety of Hybrid Tea rose plant characterized by the following combination of characteristics:

(a) from a physical point of view forms bronze green mature wood, assumes an upright to bushy growth habit, and forms attractive double flowers with consistent petals which are Vermillion Hollandais on the inside and Rouge de Carthame on the outside, and (b) from the biological point of view forms vigorous vegetation, produces flowers in abundance, exhibits the ability readily to be forced, is not particularly susceptible to diseases, and forms long lasting flowers comprising petals which detach cleanly;

substantially as herein shown and described.

* * * * *

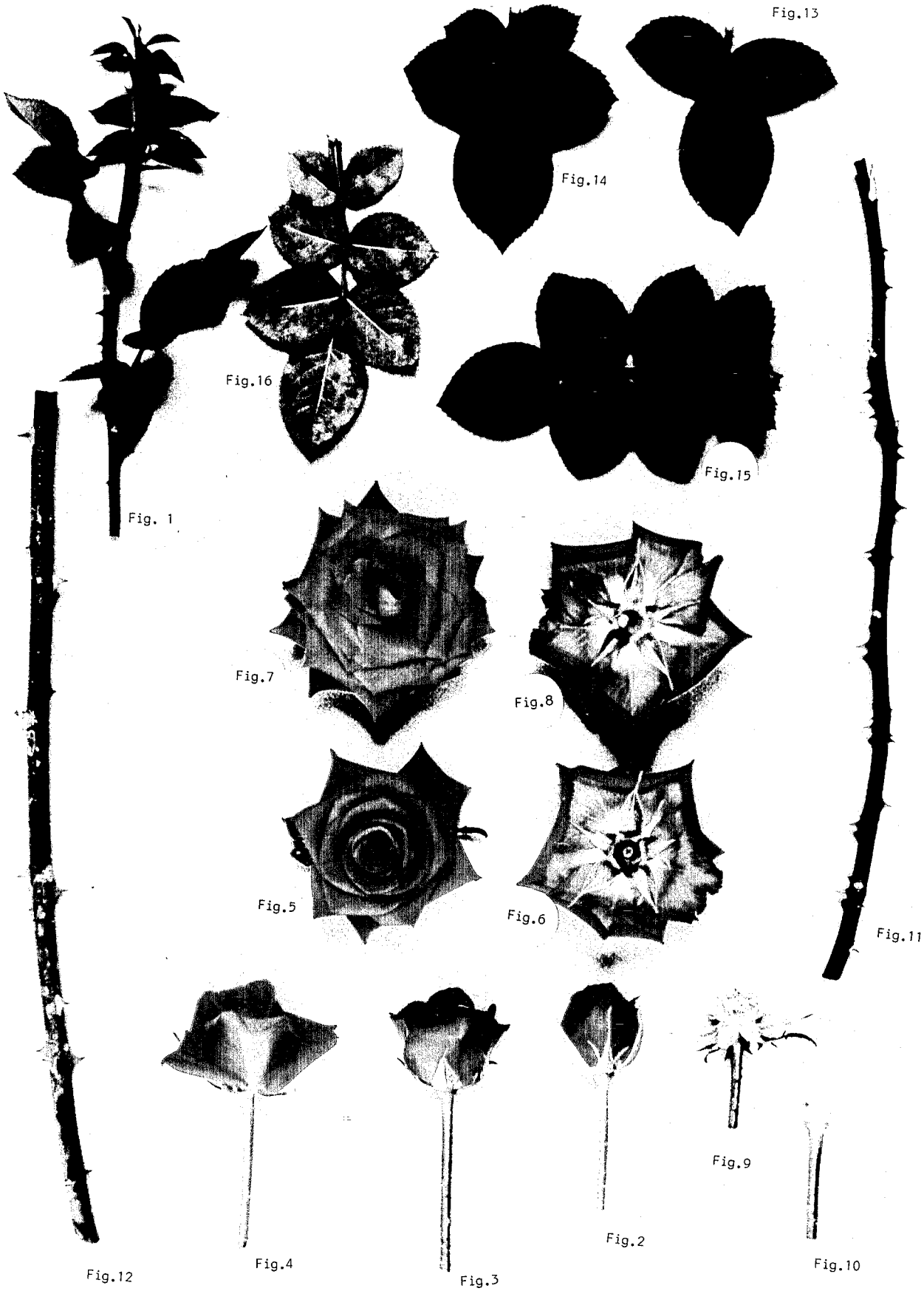

DELJACQ